US010865435B2

(12) United States Patent
Rama Rao et al.

(10) Patent No.: US 10,865,435 B2
(45) Date of Patent: Dec. 15, 2020

(54) METHOD OF SCREENING ANTIBACTERIAL COMPOUNDS AS INHIBITOR OF MFD

(71) Applicants: INSTITUT NATIONAL DE LA RECHERCHE AGRONOMIQUE, Paris (FR); CENTRE NATIONAL DE LA RECHERCHE SCIENTIFIQUE, Paris (FR); UNIVERSITE DE STRASBOURG, Strasbourg (FR)

(72) Inventors: Nalini Rama Rao, Buc (FR); Didier Rognan, Bernardswiller (FR); Didier Lereclus, Oulins (FR)

(73) Assignees: INSTITUT NATIONAL DE RECHERCHE POUR L'AGRICULTURE, Paris (FR); CENTRE NATIONAL DE LA RECHERCHE SCIENTIFIQUE, Paris (FR); UNIVERSITE DE STRASBOURG, Strasbourg (FR)

( * ) Notice: Subject to any disclaimer, the term of this patent is extended or adjusted under 35 U.S.C. 154(b) by 68 days.

(21) Appl. No.: 16/094,864

(22) PCT Filed: May 3, 2017

(86) PCT No.: PCT/EP2017/060525
§ 371 (c)(1),
(2) Date: Oct. 18, 2018

(87) PCT Pub. No.: WO2017/191184
PCT Pub. Date: Nov. 9, 2017

(65) Prior Publication Data
US 2019/0345532 A1    Nov. 14, 2019

(30) Foreign Application Priority Data
May 3, 2016  (EP) .................... 16305514

(51) Int. Cl.
*C12Q 1/18* (2006.01)
*G16B 35/20* (2019.01)
(52) U.S. Cl.
CPC .............. *C12Q 1/18* (2013.01); *G16B 35/20* (2019.02)
(58) Field of Classification Search
None
See application file for complete search history.

(56) References Cited

PUBLICATIONS

Han et al. (PLoS Pathogens. Jun. 2008 4(6): 1-12).*
International Search Report dated Jun. 20, 2017, issued in corresponding International Application No. PCT/EP2017/060525, filed May 3, 2017, 2 pages.
Written Opinion of the International Searching Authority dated Jun. 20, 2017, issued in corresponding International Application No. PCT/EP2017/060525, filed May 3, 2017, 5 pages.
Selby C.P., et al., "Structure and function of transcription-repair coupling factor. II. Catalytic properties," Journal of Biological Chemistry 270(9):4890-4895, Mar. 3, 1995.
Han, J., et al., "Key role of Mfd in the development of fluoroquinolone resistance in Campylobacter jejuni," PLOS Pathogens 4(6):e1000083, Jun. 2008.
Roberts, J., et al., "Mfd, the bacterial transcription repair coupling factor: translocation, repair and termination," Current Opinion in Microbiology 7(2):120-125, Apr. 2004. Abstract.
Witkin, E.M., "Mutation frequency decline revisited," Bioessays 16(6):437-444, Jun. 1994.
Kurthkoti, K., et al., "Base excision and nucleotide excision repair pathways in mycobacteria," Tuberculosis 91(6):533-543, Nov. 2011.
Guillemet, E., et al., "The bacterial DNA repair protein Mfd confers resistance to the host nitrogen immune response," Scientific Reports vol. 6:29349, Jul. 20, 2016, 12 pages.
International Preliminary Report on Patentability and Written Opinion dated Nov. 6, 2018, issued in corresponding International Application No. PCT/EP2017/060525, filed May 3, 2017, 6 pages.
Roberts, J., et al., "Mfd, the bacterial transcription repair coupling factor: translocation, repair and termination," Current Opinion in Microbiology 7(2):120-125, Apr. 2004.

* cited by examiner

*Primary Examiner* — Jennifer E Graser
(74) *Attorney, Agent, or Firm* — Christensen O'Connor Johnson Kindness PLLC

(57) ABSTRACT

Embodiments of the present disclosure relate to methods of screening and optionally designing compounds as inhibitors of Mfd (Mutation Frequency Decline), such compounds being useful for the treatment of bacterial infections. Embodiments of the methods include culturing pathogenic bacteria expressing functional Mfd with various concentrations of 1 mM or less, incubating the cultures with and without nitric oxide stress conditions, evaluating bacterial survival in each of the cultures, and calculating the concentration of the molecule required to decrease by 50% the survival rate of the bacteria (IC50) by comparing the cfu of the untreated cultures and cultures following nitric oxide stress.

Figure 1:
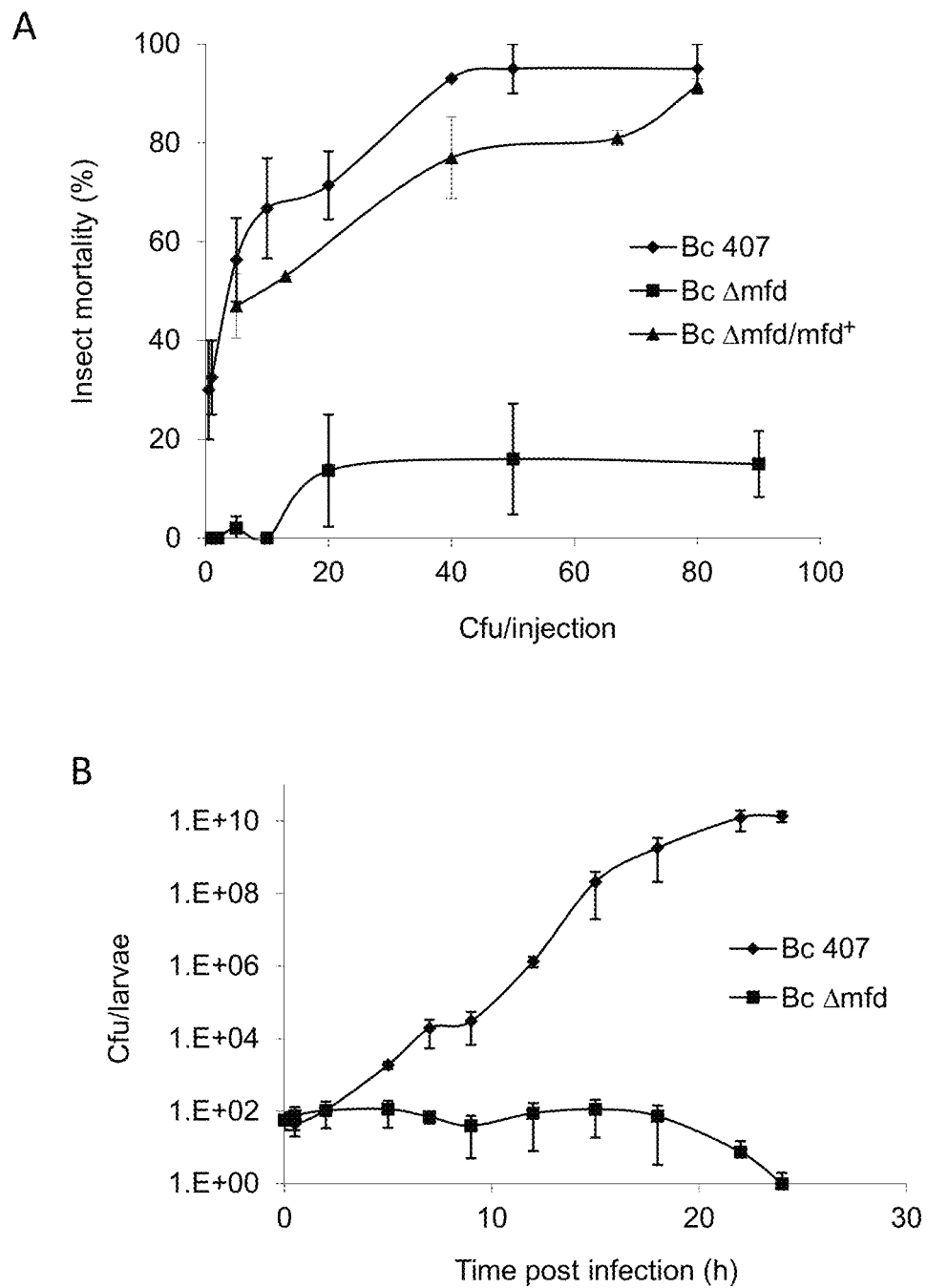

6 Claims, 4 Drawing Sheets
Specification includes a Sequence Listing.

SEQUENCE LISTING

<160> NUMBER OF SEQ ID NOS: 18

<210> SEQ ID NO 1
<211> LENGTH: 28
<212> TYPE: DNA
<213> ORGANISM: bacillus cereus

<400> SEQUENCE: 1
cgcggatccg taggctccat taacgcag 28

<210> SEQ ID NO 2
<211> LENGTH: 30
<212> TYPE: DNA
<213> ORGANISM: bacillus cereus

<400> SEQUENCE: 2
gctctagaca ccaagtaacg ccactaaatc 30

<210> SEQ ID NO 3
<211> LENGTH: 29
<212> TYPE: DNA
<213> ORGANISM: bacillus cereus

<400> SEQUENCE: 3
aactgcagga ggtgtttctg caattgagg 29

<210> SEQ ID NO 4
<211> LENGTH: 27
<212> TYPE: DNA
<213> ORGANISM: bacillus cereus

<400> SEQUENCE: 4
ccggaattcg ctgcctcatt tctactg 27

<210> SEQ ID NO 5
<211> LENGTH: 24
<212> TYPE: DNA
<213> ORGANISM: bacillus cereus

<400> SEQUENCE: 5
aactgcaggc agacactgcg gagg                                            24

<210> SEQ ID NO 6
<211> LENGTH: 31
<212> TYPE: DNA
<213> ORGANISM: bacillus cereus

<400> SEQUENCE: 6
tgctctagac cttcgggatt actaccctgc c                                    31

<210> SEQ ID NO 7
<211> LENGTH: 20
<212> TYPE: DNA
<213> ORGANISM: Artificial sequence
<220> FEATURE:
<223> OTHER INFORMATION: Synthetic

<400> SEQUENCE: 7
cgggtcggta attgggtttg                                                 20

<210> SEQ ID NO 8
<211> LENGTH: 20
<212> TYPE: DNA
<213> ORGANISM: Artificial sequence
<220> FEATURE:
<223> OTHER INFORMATION: Synthetic

<400> SEQUENCE: 8
gcagctgcac cagccccttg                                                 20

<210> SEQ ID NO 9
<211> LENGTH: 27
<212> TYPE: DNA
<213> ORGANISM: shigella flexneri

<400> SEQUENCE: 9
gctctagagc gctccaccag cctgctg                                         27

<210> SEQ ID NO 10
<211> LENGTH: 30
<212> TYPE: DNA
<213> ORGANISM: shigella flexneri

<400> SEQUENCE: 10
cggggtaccc cgcgcgtggc gtattcgccg                                      30

<210> SEQ ID NO 11
<211> LENGTH: 30
<212> TYPE: DNA
<213> ORGANISM: shigella flexneri

<400> SEQUENCE: 11
cgcggatccc ggcctgctgc cagatccggc                                      30

<210> SEQ ID NO 12
<211> LENGTH: 28
<212> TYPE: DNA
<213> ORGANISM: shigella flexneri

```
<400> SEQUENCE: 12
ccggaattcc gggcgcggat gtttgccg                                          28

<210> SEQ ID NO 13
<211> LENGTH: 30
<212> TYPE: DNA
<213> ORGANISM: shigella flexneri

<400> SEQUENCE: 13
cccaagctta agaggtgccg ttgcgccgcc                                        30

<210> SEQ ID NO 14
<211> LENGTH: 30
<212> TYPE: DNA
<213> ORGANISM: shigella flexneri

<400> SEQUENCE: 14
tcccccgggg ggttatccgg tccagccggc                                        30

<210> SEQ ID NO 15
<211> LENGTH: 30
<212> TYPE: DNA
<213> ORGANISM: Artificial sequence
<220> FEATURE:
<223> OTHER INFORMATION: Synthetic

<400> SEQUENCE: 15
gcaaggcgat taagttgggt aacgccaggg                                        30

<210> SEQ ID NO 16
<211> LENGTH: 30
<212> TYPE: DNA
<213> ORGANISM: Artificial sequence
<220> FEATURE:
<223> OTHER INFORMATION: Synthetic

<400> SEQUENCE: 16
ccccgcgcgt tggccgattc attaatgcag                                        30

<210> SEQ ID NO 17
<211> LENGTH: 42
<212> TYPE: DNA
<213> ORGANISM: Bombyx mori

<400> SEQUENCE: 17
attatgctga gtgatatccc tcgaagttct cgtcgtgagc ta                          42

<210> SEQ ID NO 18
<211> LENGTH: 42
<212> TYPE: DNA
<213> ORGANISM: Bombyx mori

<400> SEQUENCE: 18
taatacgact cactataggg gagaacctca ggaagatgga tc                          42
```

METHOD OF SCREENING ANTIBACTERIAL COMPOUNDS AS INHIBITOR OF MFD

The present invention relates to methods of screening and optionally designing compounds as inhibitors of Mfd (Mutation Frequency Decline), such compounds being useful for the treatment of bacterial infections.

Every year in the European Union, antimicrobial-resistant bacterial infections lead to around 25,000 deaths and an economic cost of over 1.5 billion €. Therefore, the search for new antimicrobials and antimicrobial targets is an urgent health issue. Several strategies have been proposed, including the use of antimicrobial peptides, phage or metal nanoparticles.

The host defense against bacteria is predominantly mediated by cellular immune mechanisms. Phagocytic neutrophils and macrophages infiltrate inflamed areas, where they produce an extensive array of toxic substances. The chemicals secreted include reactive oxygen and nitrogen species, which cause DNA damage and gene mutations [Amoroso A. et al. (2008) Curr Mol Pharmacol 1: 162-170; Zaki M H et al. (2005) J Pharmacol Sci 98: 117-129]. Nitric oxide (NO) is synthesized by an enzymatic reaction involving NO synthases (NOS). NOS are expressed both as constitutive enzymes, which contribute to vasorelaxation and neurotransmission, and as inducible isoforms (iNOS). Various cells including macrophages, neutrophils and epithelial cells express iNOS, and an excess of NO is produced during most types of infections. NO can damage biological molecules including proteins and nucleic acids [Akuta T et al. (2006) Nitric Oxide 14:01-108]. NO is cytotoxic and mutagenic both for various pathogens and for host cells [Zaki et al., (2005); Yoshitake J et al. (2004) J Virol 78: 8709-8719; Zhuang J C et al. (1998) Proc Natl Acad Sci USA 95: 8286-8291]. Thus, NO plays an important and complex role during infections, limiting microbial proliferation within host cells and contributing to microbial clearance. Bacteria express sensor proteins able to detect NO, and switch on the expression of enzymes that detoxify NO before it reaches lethal levels [Laver J R et al. (2010) FASEB J 24: 286-295]. In *E. coli*, a mutant deficient for the nucleotide excision repair (NER) pathway is sensitive to $HNO_2$ treatment [Sidorkina 0 et al. (1997) Mutagenesis 12: 23-28] and the base excision repair (BER) pathway protects *Salmonella* from the genotoxic effects of the host NO [Richardson A R et al. (2009) PLoS Pathog 5: e1000451]. The action of DNA glycosylases on NO-induced DNA damage results in BER intermediates, which in turn can induce homologous recombination [Spek E J et al. (2002) J Bacteriol 184: 3501-3507]. RecBCD-dependent recombinational repair also plays a role in preventing the genotoxic effects of NO. The NO sensitivity in the absence of RecBCD-dependent homologous recombination indicates that NO toxicity is due, at least partially, to the formation of DNA double-strand breaks (DSBs) [Schapiro J M et al. (2003) Proc Natl Acad Sci USA 100: 8496-8501].

Damage to DNA can affect transcription fidelity and processivity and thereby threatens cell viability. DNA lesions that block RNA polymerase (RNAP) prevent transcription. In bacteria, RNAP stalling triggers a specialized DNA repair mechanism, called transcription coupled repair (TCR) pathway.

Mfd (Mutation Frequency Decline) is an evolutionarily conserved bacterial protein involved in TCR [Roberts J et al. (2004) Curr Opin Microbiol 7: 120-125]. Mfd removes RNAP stalled by DNA damage. Mfd utilizes ATP to translocate along DNA, most likely forcing RNAP forward and ultimately dissociating it from the DNA template [Roberts J et al. (2004)]. In *E. coli*, Mfd also contains binding domains that may recruit UvrA and trigger the associated NER pathway [Deaconescu A M et al. (2006) Cell 124: 507-520]. Mfd also decreases the efficiency with which RNAP bypasses abasic sites, possibly reducing the level of transcriptional mutagenesis caused by these DNA lesions [Smith A J et al. (2008) DNA Repair (Amst) 7:1670-1679].

The Inventors have identified and characterized the bacterial protein Mfd function during host infection; they showed that NO induces bacterial DNA damage as well as mutations and that Mfd is required to prevent or repair these lesions, they demonstrated that Mfd plays an important role during pathogenesis by conferring bacterial resistance to the host NO response.

More specifically, the Inventors have shown that the bacterial Mfd protein is essential to survive the deleterious effect of the nitrogen intermediate NO; this has been demonstrated with two different human pathogens, the Gram-positive *Bacillus cereus* and the Gram-negative *Shigella flexneri*, in both cases, Mfd plays an important role in bacterial survival in the context of NO-induced stress (see example 1). As Mfd is a protein present in the majority of bacteria and absent in animals, its role in the resistance of bacteria to the host immune response makes Mfd a potential target for the development of new drugs against pathogenic infections.

The present invention thus relates to an in vitro method of screening antibacterial molecules that potentially inhibits the Mfd activity comprising the steps of:
   a—preparing several pairs of cultures of a pathogenic bacteria expressing a functional Mfd in culture media containing different concentrations of said molecule to be tested; said concentrations of molecule to be tested being inferior or equal to 1 mM;
   b—incubating one of each pair of cultures to nitric oxide stress, leaving the other culture as untreated control;
   c—evaluating the bacterial survival in each of the cultures;
   d—calculating the concentration of the molecule to be tested required to decrease by 50% the survival rate of the bacteria ($IC_{50}$) by comparing the cfu of the culture with the molecule to be tested in two conditions: untreated and following nitric oxide stress.

In one embodiment said method comprises an additional step d2 (conducted after step d) of selecting molecule showing an IC50 less or equal to 200 µM, preferably less or equal to 100 µM.

Pathogenic bacteria are bacteria that cause infection, they are preferably human pathogenic bacteria.

The recitation "expressing a functional Mfd" means that the pathogenic bacteria is able to express a Mfd protein showing an ATPase activity and/or for which Mfd is necessary to survive immune stress, in particular nitric oxide stress; in other words, a pathogenic bacteria expressing a functional Mfd that may be used in the method of screening according to the present invention survives when it is cultured in nitric oxide stress conditions.

Said pathogenic bacteria may be a Gram-positive or a Gram-negative bacteria and can be chosen amongst human pathogenic bacteria, such as *Bacillus cereus* group members, *Shigella, Salmonella, Clostridium, Staphylococcus, Klebsiella, E. coli, Neisseria, Yersinia, Listeria, Streptococcus, Mycobacterium, Clamydia* and *Helicobacter* species.

The skilled person is able to prepare an appropriate bacterial culture medium; such culture medium may be any appropriate laboratory bacterial growth medium such as LB, BHI, M17, RPMI, DMEM medium or specific growth medium according to selected pathogenic bacterial species.

Preferred culture conditions in step a) are such as the bacteria are grown until mid exponential growth phase to allow mfd gene expression. The growth conditions may vary according to pathogenic bacterial species. Usually, the bacteria will be grown at a temperature comprised between 30° C. and 37° C. with shaking, except for anaerobic bacteria (such as *Clostridium*).

The nitric oxide stress is obtained by the introduction of NO in the culture medium; NO can be artificially produced in vitro by addition of NO donors such as acidified sodium nitrite, NOR4, NOC7 or NONOate, each at concentration between 0.1 and 2 mM.

The evaluation of the bacterial survival of step c) is preferably performed by plating on agar plates the harvested bacteria obtained after incubation of step b) or by flow cytometry, or using live and dead kits.

The in vitro method of screening antibacterial molecule according to the invention allows the identification of molecules showing antibacterial activity as illustrated in Example 3. In particular, Inventors have shown that tadalafil ((6R-trans)-6-(1,3-benzodioxol-5-yl)-2,3,6,7,12,12a-hexahydro-2-methyl-pyrazino[1',2':1,6]pyrido[3,4-b]indole-1,4-dione) has antibacterial activity. The present invention thus also relates to the use of tadalafil as antibacterial agent and for the treatment of bacterial infections.

The structure of the Mfd ATP-binding site may also be used in the present invention to search, via in silico screening, for small molecules that could bind to it, prevent ATP binding and thus inhibit the function of Mfd.

Accordingly, the method according to the present invention may comprise additional preliminary steps (conducted before step a) of said method of screening) including:

a1—generating a three-dimensional model of the ATP-binding domain of Mfd using three-dimensional atomic coordinates of the ATP-binding domain of Mfd from state-of-the-art homology modelling programs [e.g. Modeller, Sali A et al. 1993, J. Mol. Biol. 234, 779-815];

a2—screening a library of physically-available small molecules for compounds, predicted by any computational method (e.g. docking, pharmacophore search, de novo design, active site comparisons; Rognan D., 2010, Mol. Inf, 29, 176-187), to occupy the ATP-binding site;

a3—selecting the most interesting virtual hits according to any theoretical score (e.g. docking score, pharmacophore fitness value, predicted binding free energy, active site similarity score; Rognan D., 2010, Mol. Inf, 29, 176-187) for experimental validation.

Part 2.2 of Example 2 illustrates such in silico steps.

The potential Mfd inhibitor molecules identified with this preliminary computer-assisted method can then be tested in the in vitro method of screening of the invention.

In a preferred embodiment, the potential Mfd inhibitor molecule is selected amongst compounds fulfilling the following properties: (i) at least one hydrogen-bond donor, and/or (ii) at least two hydrogen-bond acceptors, and/or (iii) at least one aromatic ring, and/or (iv) predicted aqueous solubility higher than 50 mM, and/or (v) topological polar surface area lower than 120 Å$^2$.

In another embodiment, the specificity of the molecule identified by the in vitro method of screening of the invention may be tested towards the enzymatic activity of Mfd (ATPase). These additional steps may be conducted by:

e—incubating the Mfd protein with the molecule identified as a Mfd inhibitor using the in vitro method of screening of the invention; and f—determining whether or not the ATPase activity of Mfd is reduced relative to the activity of a Mfd that has not been incubated with said molecule.

Several methods to measure the ATPase activity may be used; among them, one typical in vitro screening method to measure the ATPase activity of a protein is the malachite green phosphate Assay (Rowlands et al. Analytical Biochemistry 327 (2004 176-183; Pegan et al. Combinatorial Chemistry & High Throughput Screening, 2010, Vol. 13, N° 1). This colorimetric assay, which can easily be performed in 96 well plates, is based on the quantification by spectrophotometry of the green complex formed between Malachite Green, molybdate and free orthophosphate. The rapid color formation from the reaction can be conveniently measured on a spectrophotometer or on a plate reader. The inhibitor molecules will be serially diluted in 96-well plates and mixed with the malachite green phosphate assay compounds. Purified Mfd proteins (purified from the relevant bacteria either from the bacteria itself or as a recombinant protein purified from a heterologous system such as *E. coli*) will be added to the plates and the colorimetric determination of ATPase activity of Mfd will be performed. For example, hits may be tested at a single concentration of 10 µM and scored for an absorbance at 620 nm reduced by more than 50% compared to the signal produced by the Mfd protein control without inhibitor. A dose response curve using at least eight increasing concentrations of the inhibitor (from 0.1 nM to 50 µM) leads to an IC50 value of the inhibitor for this particular assay.

FIGURES

FIG. 1. (A) Various doses of wild-type (Bc 407), mfd mutant (Bc Δmfd) and the complemented Bc Δmfd/mfd+ strains were injected into the hemocoel of *B. mori* larvae. Insect mortality was recorded 24 h post infection. The results are mean values of at least three independent experiments. (B) *B. mori* were infected with 50 cfu of *B. cereus* wild-type (Bc 407) or mfd mutant (Bc Δmfd) strains. After the indicated times, larvae were crushed in PBS medium and cfu were counted by plating serial dilutions on agar plates. The results reported are mean values of at least five independent experiments.

Figure 2:
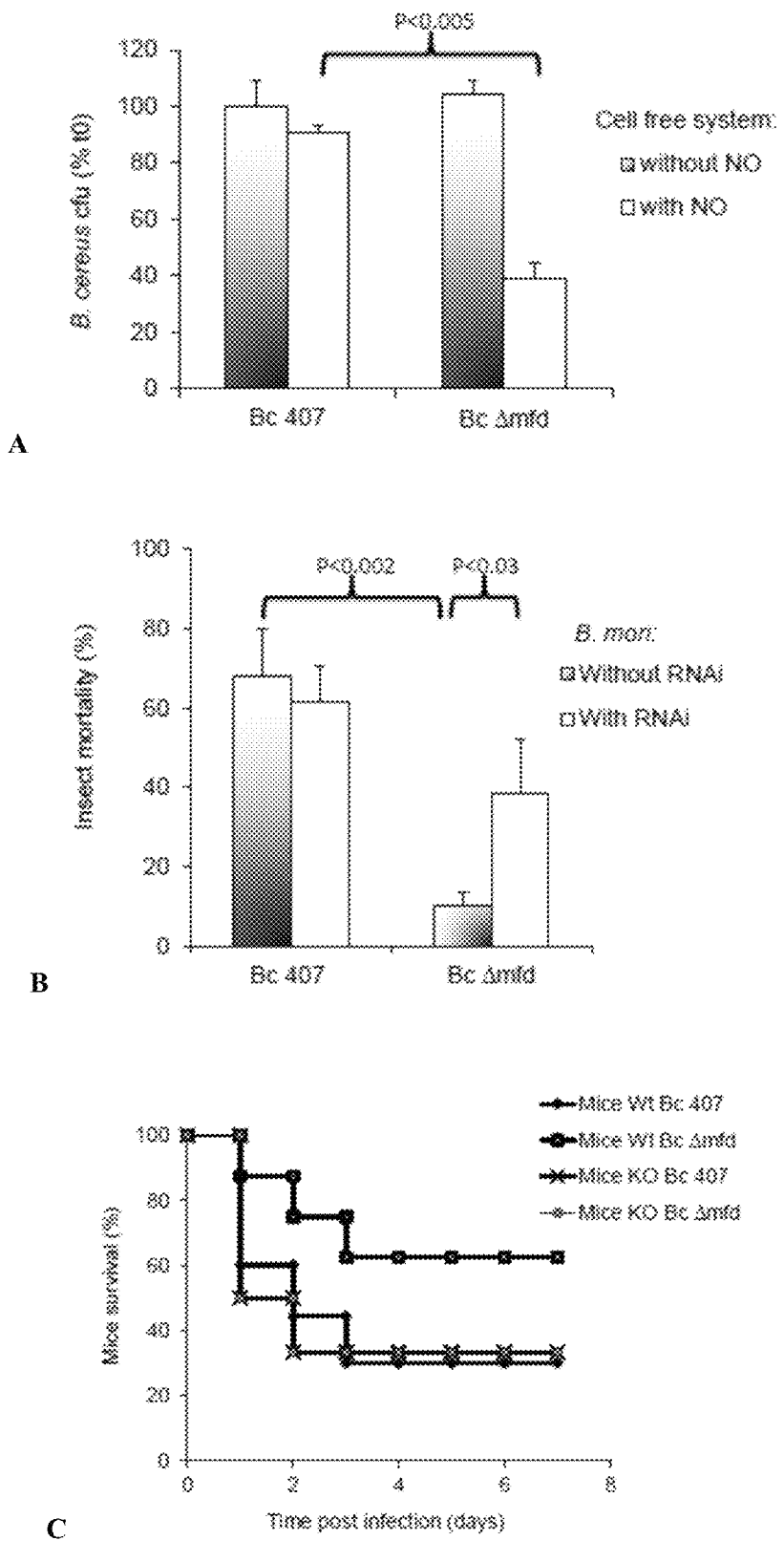

FIG. 2. (A) *B. cereus* bacteria were exposed directly to chemically generated NO (1.5 mM sodium nitrite) for 1 h in a cell-free system. Bacteria were then harvested and plated on agar plates to evaluate bacterial survival. Cfu counts were normalized to initial cfu. The results reported are mean values of at least five independent experiments. (B) NO production in the insect *B. mori* was silenced by RNA interference (RNAi). Larvae injected with either 1 µg of double-stranded NOS RNA (dsRNA) or water only (control) were infected with either wild-type *B. cereus* or the Δmfd mutant and insect mortality was recorded after 24 h. (C) C57/Bl6/Sev129 mice (Mice wt) and NOS2−/− mice (KO Mice) were inoculated intranasally with *B. cereus* wild-type and Δmfd mutant strains (5.10$^6$ cfu/mice). Mortality was recorded daily for 7 days.

Figure 3:
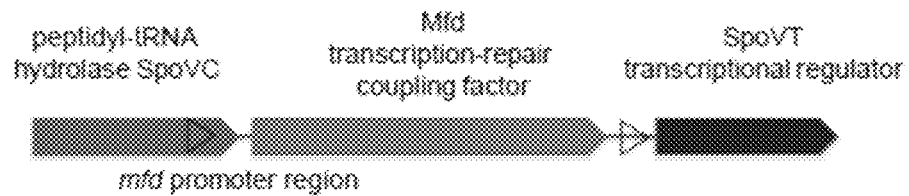

FIG. 3. mfd gene environment in *Bacilli* is schematically represented. The promoter region as defined in http://genome.jouy.inrafr/cgibin/seb/viewdetail.py?id=mfd_60430_63963_1 is indicated as black arrow.

Figure 4:
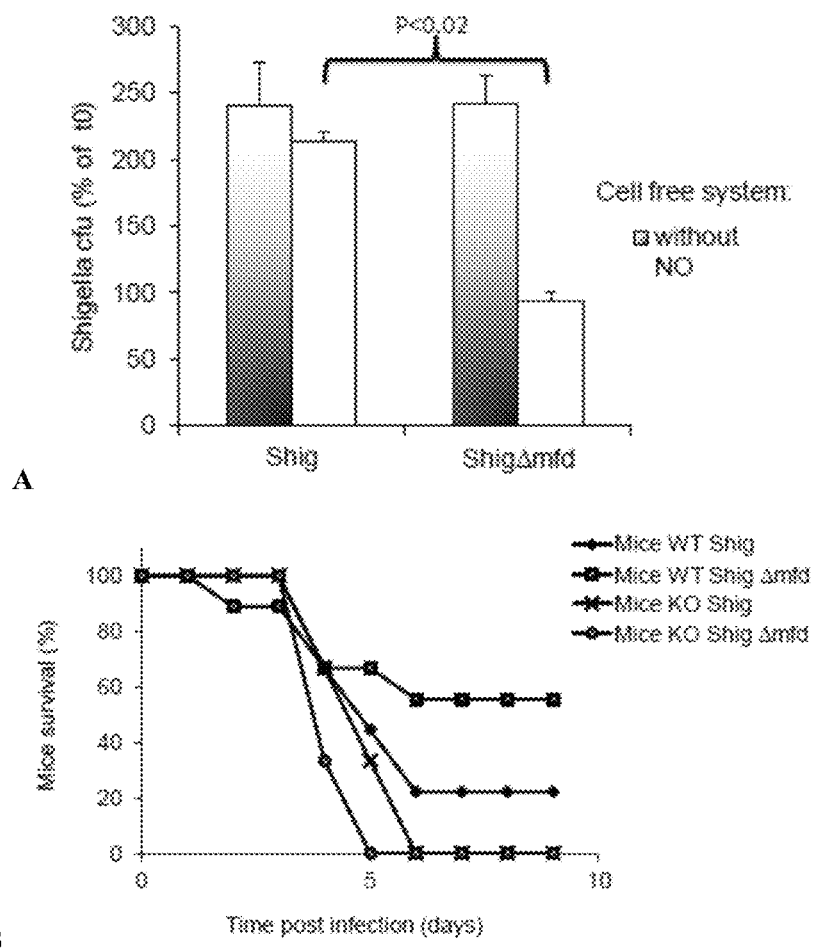

FIG. 4. (A) *S. flexneri* bacteria were exposed to chemically generated NO (500 μM sodium nitrite) for 4 h in a cell-free system. Bacteria were harvested and plated on agar plates to evaluate bacterial survival. Cfu counts were normalized to initial cfu at t0.

(B) C57/Bl6/Sev 129 mice (Mice wt) and NOS2−/− mice (Mice KO) were inoculated intranasally with *S. flexneri* wild-type and Δmfd mutant bacteria ($10^7$ cfu/mice). Mortality was recorded daily for 9 days.

Figure 5:
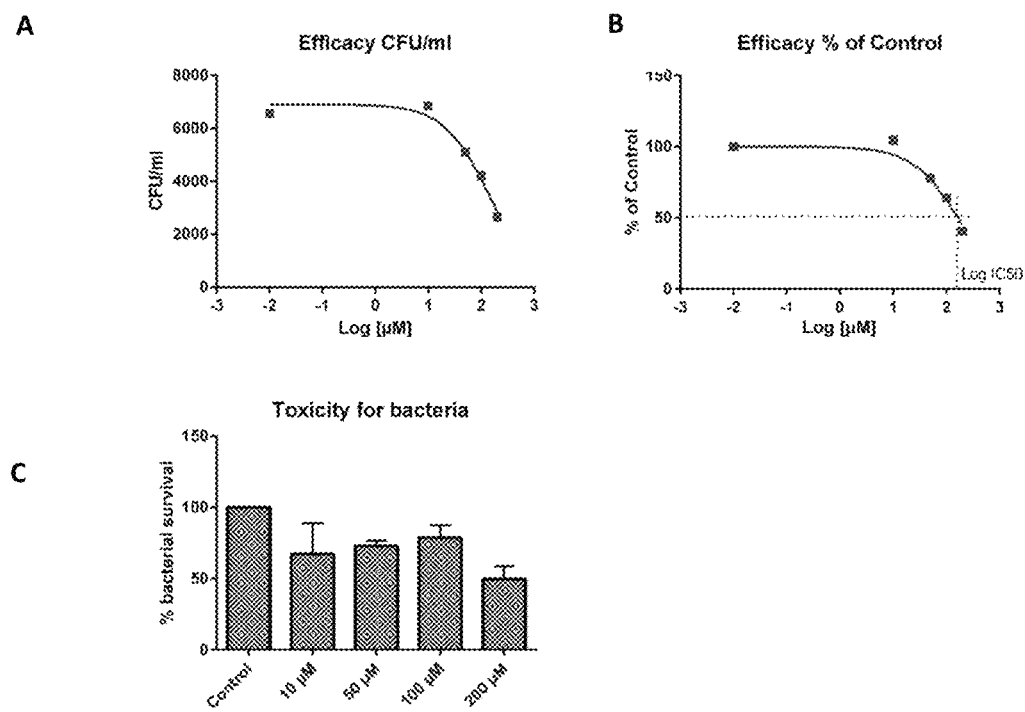

FIG. 5. Activity of a molecule, Tadalafil, capable of inhibiting bacterial growth in the presence of NO.

Figure 6:
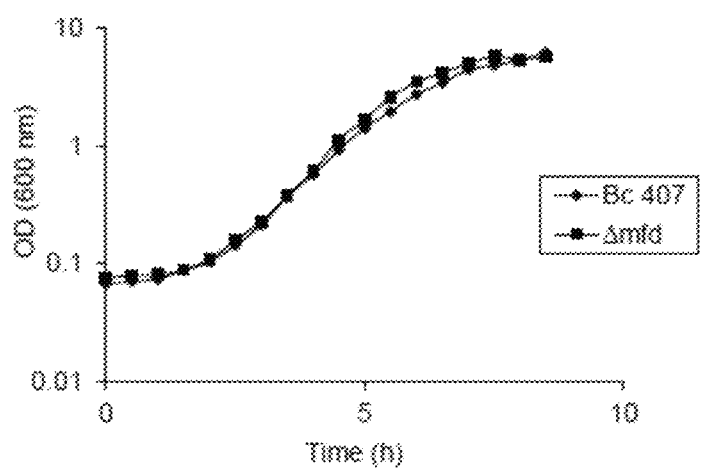

FIG. 6. *B. cereus* wild type and Δmfd mutant strains were inoculated in LB medium at a starting optical density (OD) of 0.07 and grown at 25° C. with agitation. The OD was measured every hour at 600 nm. This graph represents representative growth curves out of at least five independent experiments.

EXAMPLES

Example 1—Determination of the Role of Mfd for Virulence and Bacterial Growth In Vivo 1.A. Materials and Methods
Bacterial Strain and Mutant Construction

*Bacillus cereus* mutant: The Bc 407 Δmfd mutant was constructed as follows. The mfd gene was disrupted through double homologous recombination using the thermosensitive vector pMAD. BamHI-XbaI (515 bp) and PstI-EcoRI (512 bp) DNA fragments corresponding to upstream and downstream regions of the mfd gene were generated from the Bc 407 chromosome by PCR using the primer pairs:

```
                                    [SEQ. ID. No 1]
mfd-1 (5'-CGCGGATCCGTAGGCTCCATTAACGCAG-3'),

[SEQ. ID. No 2]
mfd-2 (5'-GCTCTAGACACCAAGTAACGCCACTAAATC-3'),

[SEQ. ID. No 3]
mfd-3 (5'-AACTGCAGGAGGTGTTTCTGCAATTGAGG-3'),

[SEQ. ID. No 4]
mfd-4 (5'-CCGGAATTCGCTGCCTCATTTCTACTG-3').
```

A KanR cassette carrying a kan gene was purified from pDG783 [Sanchis V et al. (1996) J Biotechnol 48:81-96] as a 1.6 Kb XbaI-PstI fragment. The amplified DNA fragments were digested with the appropriate enzymes and inserted between the BamHI and EcoRI sites of pMAD. The resulting plasmid was introduced into Bc 407 by electroporation [Arantes O et al. (1991) Gene 108:115-119] and the mfd gene was deleted by a double crossover event as previously described [Lereclus D et al. (1992) Mol Microbiol 7:35-46]. Chromosomal allele exchange was confirmed by PCR with oligonucleotide primers located upstream from mfd-1, mfd-5 (5'-AACTGCAGGCAGACACTGCGGAGG-3') [SEQ. ID. N° 5] and downstream from mfd-4, mfd-6 (5'-TGCTCTAGACCTTCGGGATTACTACCCTGCC-3') [SEQ. ID. N° 6], and in the KanR cassette (5'-CGGGTCGGTAATTGGGTTTG-3') [SEQ. ID. N° 7], (5'-GCAGCTGCACCAGCCCCTTG-3') [SEQ. ID. N° 8]. The insertion mutant strain was designated Bc 407 Δmfd.

To complement the Bc 407 Δmfd mutant, the mfd gene, including the coding sequence and the promoter region (FIG. 3A and http://subtiwiki.uni-goettingen.de/wiki/index-.php), was obtained using the primer pair mfd-5 and mfd-6, and the sequence of the obtained fragment was verified. The pHT315 vector containing the complete mfd gene and its promoter was used to transform Bc 407 Δmfd strain by electroporation. Transformants were selected for resistance to erythromycin. The resulting new strain was designated Bc 407 Δmfd/mfd+.

The *Shigella flexneri* 2a M90T strain was used as the wild-type reference strain. A Δmfd mutant of this strain was constructed as follows. The mfd gene (S1198) was interrupted by double recombination as previously described [Menard R et al. (1994) EMBO J 13:5293-5302]. Upstream and downstream regions of the mfd gene were generated from the *S. flexneri* 2a M90T chromosome by PCR using the primer pairs:

```
                                    [SEQ. ID. No 9]
S-mfd-1 (5'-GCTCTAGAGCGCTCCACCAGCCTGCTG-3'),

[SEQ. ID. No 10]
S-mfd-2 (5'-CGGGGTACCCCGCGCGTGGCGTATTCGCCG-3'),

[SEQ. ID. No 11]
S-mfd-3 (5'-CGCGGATCCCGGCCTGCTGCCAGATCCGGC-3')
and

[SEQ. ID. No 12]
S-mfd-4 (5'-CCGGAATTCCGGGCGCGGATGTTTGCCG-3').
```

A KanR cassette carrying a kan gene was excised from pUC18 K2 as a 839 bp fragment. The DNA fragments were digested with the appropriate enzymes and inserted into pGP704 [Menard R et al. (1994)]. The resulting plasmid was introduced into M90T by electroporation and the mfd gene was deleted by a double crossover event.

Chromosomal allele exchange was confirmed by PCR with oligonucleotide primers located upstream from S-mfd-1, S-mfd-5 (5'-CCCAAGCT-TAAGAGGTGCCGTTGCGCCGCC-3') [SEQ. ID. N° 13] and downstream from S-mfd-4, S-mfd-6 (5'-TCCCCCGGGGGGTTATCCGGTCCAGCCGGC-3') [SEQ. ID. N° 14], and in the KanR cassette (5'-GCAAGGC-GATTAAGTTGGGTAACGCCAGGG-3') [SEQ. ID. N° 15], (5'-CCCCGCGCGTTGGCCGATTCATTAATGCAG-3') [SEQ. ID. N° 16]. The insertion mutant strain was designated *S. flexneri* Δmfd. Growth curves of wild type and mutant strain were similar in LB or RPMI medium at 37° C.

NO Inducer and Inhibitor

Bacteria were exposed directly to chemically generated NO in a cell-free system as described by Miyagi et al. [Miyagi K et al. (1997) Infect Immun 65: 4108-4113] with modifications. Briefly, bacteria were grown in LB medium until mid exponential growth phase at 37° C. with shaking. Cultures were then diluted to $10^4$ cfu/ml in RPMI-1640 medium (Invitrogen) at acidic pH (pH 5.4) in the presence of 0 to 10 mM sodium nitrite (Walco Pure Chemical Industries Ltd); under these acidic conditions, NO is generated from the sodium nitrite by a chemical reaction [Miyagi K et al. (1997)]. The bacteria were then cultured at 37° C. for 0 to 4 h, harvested and plated on agar plates to evaluate bacterial survival. Using this cell free assay, the NO concentration required to decrease by 50% the survival rate of each strain (IC50) was calculated using the GraphPad PRISM software (version 6.0, GraphPad Software, San Diego, Calif.) with non-linear regression.

To inhibit the nitrogen response in cellular assay, the NO inhibitor NMMLA NG monomethyl-L-arginine (Sigma) was used at 1 mM.

Insects and In Vivo Experiments Bombyx mori larvae were infected by injection into the hemolymph as described elsewhere [Ramarao N et al. (2012) J Vis Exp 70: 4392; Salamitou S et al. (2000) Microbiology 146: 2825-2832.]. Groups of 20 last-instar larvae (same weight) were injected at the base of their last proleg with 10 µL of suspensions containing various doses of vegetative bacteria. Insect mortality was recorded after 24 h at 25° C. To estimate the number of bacteria in living or dead larvae, the insect larvae were crushed and homogenized in sterile water; dilutions were plated onto LB agar plates [Guillemet E et al. (2010) J Bacteriol 192: 286-294.6; Tran S L et al. (2010) J Bacteriol 192: 2638-2642].

RNAi in Insects

NO production can be silenced at the transcription level by using RNA interference (RNAi) [Novina C D, Sharp P A (2004) Nature 430: 161-164]. The silencing of gene expression by double-stranded RNA molecules is very efficient in B. mori [Kanginakudru S et al. (2007) Insect Mol Biol 16: 635-644.], and the gene coding for the inducible nitric oxide synthase-like protein (iNOS548LP) is present in only a single copy (in contrast to other invertebrate immune mechanisms for which many genes are present in several copies). Thus, RNAi is a powerful tool for manipulating NO levels in infected B. mori [Rivero A (2006) Trends Parasitol 22: 219-225]. Double-stranded RNA (dsRNA) was produced from genomic DNA of B. mori using the primers 5'-ATTATGCTGAGTGATATCCCTCGAAGTTCTCGT CGTGAGCTA-3' [SEQ. ID. N° 17] and 5'-TAATACGACT-CACTATAGGGGAGAACCTCAGGAAGATGGATC-3' [SEQ. ID. N° 18] and the Megascript RNAi Kit (Ambion). Larvae injected with either 1 µg of double-stranded NOS RNA (dsRNA) or water only (control) were infected with either wild-type Bc 407 or the Δmfd mutant (50 cfu/larvae) and mortality was recorded after 24 h.

Mouse Experiments

Mice experiments were performed by INRA-UIERP animal facilities in Jouy en Josas, France. C57/BL6/Sev129 mice, aged 6- to 8-weeks old were used for infections. Wild-type mice were obtained from Elevage Janvier, France. Mice with a targeted disruption of the NOS-2 gene, generated as previously described [MacMicking J D et al. (1995) Cell 81: 641-650] were generously supplied by Drs. J. D. MacMicking, C. Nathan (Cornell University Medical College, New York) and Jean Claude Jeanny, Institut des Cordeliers, animalerie centrale de la faculté de Pharmacie de Paris (health monitoring report from Harlan UK Technical service). PCR with DNA from tail biopsies was used for genotyping to verify the presence or absence of the NOS-2 gene [Thillaye-Goldenberg et al. (2000) J Neuroimmunol 110: 31-44]. Groups of 9 to 10 mice were inoculated intranasally with wild type or mutant bacteria (5.10$^6$ cfu/mouse for B. cereus, and 10$^7$ cfu/mouse for Shigella strains) as described in [Tran S L et al. (2011) Cell Microbiol 13: 92-108]. Mortality was recorded daily for 7-9 days.

1.B. Results

Mfd is Required for Virulence and Bacterial Growth In Vivo

A stable mfd deletion strain was constructed by insertion of a kanamycin-resistance cassette into the mfd gene. B. cereus growth of wild-type and Δmfd mutant strains did not differ in LB medium (FIG. 6). The pathogenicity of the wild type and mutant strains was tested in *B. mori* (FIG. 1A). Deletion of mfd induced a drastic loss of virulence compared to the wild-type strain. To confirm that the chromosomal deletion did not induce a polar effect, the mfd mutant strain was genetically complemented by introduction of a plasmid carrying a functional mfd gene and the corresponding promoter region (FIG. 3). Complementation of the Δmfd strain by the mfd+ gene restored the wild-type virulence phenotype (FIG. 1A).

This finding shows that Mfd is required for *B. cereus* virulence in an insect model of infection.

The survival of the strains during infection has been assessed by crushing the insects and dilution plating. In sharp contrast to the wild type stain, the Δmfd mutant was unable to grow in vivo and no bacteria were recovered 24 h after infection (FIG. 1B). Thus, Mfd is required for bacterial survival during the infectious process.

Mfd is Required for *B. cereus* Resistance to NO Stress

It has then been tested whether the failure of the Δmfd mutant to survive in the insect and mammal host was due to its sensitivity to host cellular defenses.

In this experiment, bacteria were first exposed directly to chemically generated NO in a cell-free system (FIG. 2A). The wild-type strain survived, whereas survival of the Δmfd mutant was strongly impaired (P<0.005). The concentration of NO able to reduce by 50% the survival of the strains (IC 50) was measured by dose-response experiments (Table 1). The NO-IC 50 required for the wild type strain was 2.5 times higher than the IC 50 of the mfd mutant. These data implicate Mfd in the resistance to NO, a critical mediator of the host innate immune response.

TABLE 1

| | IC 50 (mM NO) | Error to the mean |
|---|---|---|
| Bc 407 | 4, 12 | 1, 2 |
| Δmfd | 1, 16 | 1, 3 |

Then, to determine whether the mfd mutant growth was inversely correlated with the host NO response in vivo, we used two animal models: *B. mori* larvae and mice. NO production in insects was shut down by injection of NOS-siRNA into the insect hemocoel prior to infection with wild-type and mfd mutant strains. Inhibition of NO production had no significant effect on insect mortality after infection by the wild-type strain, indicating that this strain counteracts the NO host defense (FIG. 2B). In contrast, inhibition of NO production significantly increased the virulence of the Δmfd strain compared with insects producing an NO-response (P<0.03). Thus, Mfd is essential for virulence in the context of NO-stress in vivo. The mortality induced by the mfd mutant in the context of NO inhibition was intermediate and did not reach the level of mortality induced by the wild type strain (P>0.067) indicating that some other lesions, independent of NO, may also be dealt with by Mfd.

Wild-type and Δmfd strain virulence was also assessed in wild-type mice and in mice deficient for NO production (iNOS-KO) (FIG. 2C). The percentage of surviving wild-type mice infected with the *B. cereus* wild type strain decreased sharply following infection, while the survival of wild-type mice infected with the Δmfd mutant was significantly higher. These results show that Mfd makes a substantial contribution to *B. cereus* pathogenesis in a mammalian model of infection. The survival of iNOS-KO mice infected with wild type and Δmfd mutant strains was similar to the survival of the wild-type mice infected with the wild type strain. Thus, in the absence of NO production, the mfd deletion had no effect on virulence. These findings imply that Mfd counteracts the deleterious effect of NO on bacteria in vivo.

This study as a whole provides significant insights into the previously undescribed role of Mfd during bacterial pathogenesis and, in particular, demonstrates its involvement in the mechanisms of defense against NO stress in vivo.

Mfd as a Universal Virulence Factor Implicated in NO Stress Resistance

To determine whether mfd inactivation affects virulence in another bacterial species, the effect of mfd deletion in *Shigella flexneri* has been studied.

*S. flexneri* is a Gram-negative *Bacillus* and is the major etiological agent of dysentery in developing countries [Zychlinsky A et al. (1992) Nature 358: 167-169; Sansonetti P J et al. (2007) Immunity 26: 149-161]. NO is produced following *S. flexneri* infection but does not result in clearance of *S. flexneri* from infected mice, suggesting that bacteria escape the NO response [Way S S et al. (1998) Infect Immun 66: 3012-3016].

To study the role of Mfd in the resistance of *Shigella* to NO stress, survival of the Δmfd mutant was tested in NO stress conditions in a cell-free system (FIG. 4A). The growth of the *Shigella* Δmfd mutant in the presence of NO was much weaker than that of the wild-type strain (P<0.02). The survival of the wild type and mutant *S. flexneri* strains in the cell free system without NO exposure was identical (FIG. 4A).

The role of Mfd in resistance to NO stress was also tested in vivo in wild type and NOS-KO mice (FIG. 4B). Survival of wild-type mice infected with the Δmfd mutant was significantly higher than survival of these mice infected with the wild-type *Shigella* strain. Thus, Mfd is required for full *Shigella* virulence. In mice deficient for NO production, both wild type and Δmfd mutant strains were highly virulent, and mouse survival was even lower than for wild type mice.

These experiments demonstrate that Mfd plays an important role in promoting bacterial survival in the context of NO-stress during the infection process of two very divergent bacteria.

Example 2—Identification of Inhibitors of the Function of the Bacterial Protein Mfd (Mutation Frequency Decline)

The previous assays show that Mfd allows bacterial survival and growth despite the production of toxic compounds (ie, nitrite oxide (NO)) by the host immune system.

The purpose of the present assays is to identify Mfd inhibitors and test their efficacy as antimicrobials.

Protocols:
1—Test of the molecule capacity to inhibit bacterial growth in the presence of artificially produced nitric oxide (NO);
2—Facultative step to reduce the amount of molecules to be tested: choose the molecules according to an in silico screening based on the 3D structure of Mfd;
3—Facultative step to test the specificity of the inhibitors towards the enzymatic activity of Mfd (ATPase).

2.1—Molecule Capacity to Inhibit Bacterial Growth in the Presence of Artificially Produced Nitric Oxide (NO)

Bacteria (*Bacillus cereus* strain Bc 407) were grown in LB medium until mid exponential growth phase at 37° C. with shaking. Cultures were then diluted to $10^4$ cfu/ml in PBS (Phosphate Buffered Saline, Sigma). The molecules to be tested (potential Mfd inhibitors) are added at a concentration of 0 to 1 mM to the bacteria and the bacteria+inhibitors are incubated at room temperature for 1 h without agitation.

Bacteria were then exposed directly to chemically generated NO+ in a cell-free system as described by Miyagi et al. (Miyagi et al., 1997) with modifications. Briefly, $10^4$ bacterial cfu (+various concentrations of potential Mfd inhibitors) are incubated in RPMI-1640 medium (Invitrogen) at acidic pH (pH 5.4) either in the absence or in the presence of 1.5 mM sodium nitrite (Walco Pure Chemical Industries Ltd) at 37° C. for 1 h under shaking; under these acidic conditions, NO+ is generated from the sodium nitrite by a chemical reaction (Miyagi et al., 1997).

The bacteria are harvested and plated on agar plates to evaluate bacterial survival. The cfu obtained without nitric oxide stress gives the toxicity value whereas the cfu obtained following nitric oxide stress gives the inhibitor efficacy value. Using this cell free assay, the inhibitor concentration required to decrease by 50% the survival rate of the bacteria ($IC_{50}$) in the presence of nitric oxide stress compared to untreated bacteria is calculated using the GraphPad PRISM software (version 6.0, GraphPad Software, San Diego, Calif.) with non-linear regression.

2.2—Virtual Screening Procedure for Identifying Mfd Inhibitors

Mfd Protein Structure Preparation:

The nucleotide-bound active form of *E. coli* Mfd was obtained by morphing the *E. coli* Mfd inactive form (PDB identifier 2EY5) into the active form of an Mfd homolog (RecG) in *T. maritima* (PDB identifier 1GM5), using standard settings of the Yale Morph2 server (http://morph2.molmovdb.org/submit.html).

Compound Collection Preparation:

The Bioinfo-DB database (http://bioinfo-pharma.u-strasbg.fr/bioinfo) is an in-house developed database of 4.8 million commercially available compounds as powder (1-50 mg) and filtered according to internal rules to contain drug-like compounds only. The database was first filtered to keep compounds resembling grossly to nucleotides and fulfilling the following properties: (i) at least one hydrogen-bond donor, (ii) at least two hydrogen-bond acceptors, (iii) at least one aromatic ring, (iv) predicted aqueous solubility higher than 50 mM (predicted with PipelinePilot 9.5, BIOVIA, Paris), (v) topological polar surface area lower than 120 Å$^2$. The filtered set of 1.2 million compounds was then converted in three dimensional space using Corina (Molecular Networks, Erlangen, Germany). Up to 4 stereoisomers were created in case of the presence of undefined stereocenters. When the stereocenter was explicitly defined, it was kept unchanged. Altogether, 3D atomic coordinates were defined for 1874034 compounds thereby constituting the docking set.

Docking:

The docking set (1.8 million compounds) was docked to the nucleotide-binding site of *E. coli* Mfd (Phe599, Thr602, Gln605, Gly631, Phe632, Gly633, Lys634, Thr635) with the Surflex-Dock program (Jain, J. Med. Chem., 2003, 46, 499-511). A "protomol" was first generated from the list of binding site residues (see above definition). Compounds were then docked with default settings (excepted for the –pgeom option) of the docking engine, keeping the best 10 poses, according to the native Surflex-Dock scoring function.

Hit Selection:

Potential hits were selected according to the following two strategies:

Strategy A:

The 178 best scoring poses (Surflex-Dock score>10) from the docking set were retained. Then compound redundancy was removed (high score retained if more than 2 poses originating from the same compounds) to yield 91 compounds. A chemical diversity selection by maximum common substructures was done using the LibMCS algorithm (ChemAxon Ltd., Budapest, Hungary) to retain a first set (SET1) of 23 chemically diverse compounds.

Strategy B:

All poses from the docking set were submitted to an interaction-based filter (Marcou et al. J. Chem. Inf. Model., 2007, 47, 195-207) to select 206 non-redundant compounds verifying absolutely the following interactions: hydrogen bond to Gln605.OE1 atom, hydrogen bond to Gln605.NE2 atom, hydrogen-bond to Gly631.N atom, p-p aromatic stacking to Phe599. In case of multiple poses from the same compound verifying the interaction similarity filter, the top scored posed (best Surflex-Dock score) was kept. A chemical diversity selection by maximum common substructures was done using the LibMCS algorithm (ChemAxon Ltd., Budapest, Hungary) to retain a second set (SET2) of 23 chemically diverse compounds.

Previously defined SET1 and SET2 were merged to yield a final selection of 95 compounds (two hits were common to both sets) that were further purchased in 5 mg quantities.

Example 3—Example of Molecule Capable of Inhibiting Bacterial Growth in the Presence of NO: Tadalafil Tadalafil, (6R-trans)-6-(1,3-benzodioxol-5-yl)-2,3,6,7,12, 12a-hexahydro-2-methyl-pyrazino[1',2':1,6]pyrido[3,4]-Mindole-1,4-dione ($C_{22}H_{19}N_3O_4$), is known as a type 5 phosphodiesterase inhibitor (Rotella, Nature, 2002, 1, 674-681); it has the following chemical structure:

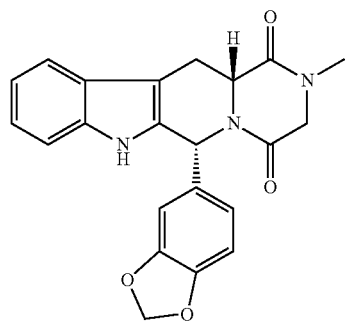 [SMILES: CN1CC(=O)N2[C@H](c3ccc4c(c3)OCO4)c3[nH]c4ccccc4c3C[C@@H]2C1=O]

This compound shows
1—a weak activity on *B. cereus* survival without stress until 100 μM (toxicity) and
2—an activity on *B. cereus* survival with nitric oxide (NO) stress at 100 µM.

Using the cell free assay described above, the tadalafil concentration required to decrease by 50% the survival rate of the bacteria ($IC_{50}$) in the presence of nitric oxide stress compared to untreated bacteria is calculated using the GraphPad PRISM software: IC50=98,67 µM (mean of two experiments) (see FIG. 5).

The invention claimed is:

1. An in vitro method of screening an antibacterial molecule that inhibits mutation frequency decline (Mfd peptide) activity comprising the steps of:
   (a) preparing several pairs of cultures of a pathogenic bacteria expressing a functional Mfd in culture media containing different concentrations of said molecule to be tested; wherein said concentrations of molecule to be tested are less than or equal to 1 mM;
   (b) incubating one of each pair of cultures in nitric oxide stress conditions obtained by addition of NO donors in said culture media, leaving the other culture of each pair untreated;
   (c) evaluating the bacterial survival in each of the cultures;
   (d) calculating the concentration of the molecule to be tested required to decrease by 50% the survival rate of the bacteria (IC50) by comparing the cfu of the culture with the molecule to be tested in two conditions: untreated and following nitric oxide stress;

(d2) selecting the molecule showing an IC50 less or equal to 200 µM;

(e) incubating the Mfd peptide with the molecule identified as a Mfd inhibitor;

(f) determining whether or not the ATPase activity of Mfd is reduced relative to the activity of a Mfd that has not been contacted with said molecule.

2. The in vitro method of screening an antibacterial molecule according to claim 1, wherein said pathogenic bacteria is a Gram-positive or a Gram-negative human pathogenic bacteria.

3. The in vitro method of screening an antibacterial molecule according to claim 1, wherein said nitric oxide stress is artificially produced in vitro by addition of NO donors at concentration between 0.1 and 2 mM.

4. The in vitro method of screening an antibacterial molecule according to claim 1, wherein the evaluation of the bacterial survival of step (c) is performed by plating on agar plates the harvested bacteria obtained after incubation of step (b), by flow cytometry, or by using a live and dead kit.

5. The in vitro method of screening an antibacterial molecule that inhibits the Mfd activity according to claim 1, comprising additional steps prior to said step (a) consisting of in silico screening for potential Mfd inhibitors including:

(a1) generating using a homology modelling program to generate a three-dimensional model of the ATP-binding domain of Mfd using three-dimensional atomic coordinates of the ATP-binding domain of Mfd;

(a2) screening a library of physically-available small molecules for compounds predicted to occupy the ATP-binding site by a docking computational method, a pharmacophore search computational method, a de novo design method, or an active site comparison method; and (a3) selecting virtual hits for experimental validation according to a docking score, a pharmacophore fitness value, a predicted binding free energy, or an active site similarity score.

6. The in vitro method of screening an antibacterial molecule according to claim 2, wherein the human pathogenic bacteria is selected from *Bacillus cereus* group members, *Shigella, Salmonella, Clostridium, Staphylococcus, Klebsiella, E. coli, Neisseria, Yersinia, Listeria, Streptococcus, Mycobacterium, Clamydia* and *Helicobacter* species.

* * * * *